United States Patent [19]

Harrington et al.

[11] Patent Number: 4,835,146

[45] Date of Patent: May 30, 1989

[54] METHOD OF TREATING SICKLE CELL ANEMIA WITH DANAZOL

[75] Inventors: William J. Harrington; Yeon S. Ahn; Ravindra Mylvaganam, all of Miami, Fla.

[73] Assignee: University of Miami, Coral Gables, Fla.

[21] Appl. No.: 59,439

[22] Filed: Jun. 8, 1987

Related U.S. Application Data

[63] Continuation-in-part of Ser. No. 936,957, Dec. 1, 1986, which is a continuation of Ser. No. 671,786, Nov. 15, 1984, abandoned.

[51] Int. Cl.$^4$ .............................................. A61K 31/58
[52] U.S. Cl. ..................................... 514/176; 514/815
[58] Field of Search ................... 514/176, 815; 540/57

Primary Examiner—Douglas W. Robinson
Assistant Examiner—Joseph A. Lipovsky
Attorney, Agent, or Firm—Cushman, Darby & Cushman

[57] ABSTRACT

Treatment of sickle cell disease using danazol.

1 Claim, No Drawings

METHOD OF TREATING SICKLE CELL ANEMIA WITH DANAZOL

This application is a continuation-in-part of Ser. No. 936,957, filed Dec. 1, 1986 which is itself a continuation of Ser. No. 671,786, filed Nov. 15, 1984 and now abandoned. The disclosure of said earlier applications Ser. No. 671,786 and No. 936,957 is incorporated herein by reference.

This invention relates to the use of danazol or an equivalent anabolic steroid in the treatment of hemolytic anemias, particularly sickle cell disease.

Said earlier applications disclose the use of danazol, a known material, in the treatment of various disorders including hemolytic anemias. The present disclosure is concerned primarily with the treatment of one such form of hemolytic anemia, namely, sickle cell anemia, which has become of particular concern in recent years.

Sickle cell anemia is a common genetic disorder characterized by anemia, painful crises involving joints, bones, the abdomen and other viscera. It is due to an abnormal hemoglobin that distorts the shape of the affected patient's red blood cells impairing their passage through small blood vessels, leading to minute occlusions (microinfarcts) which not only cause pain and shorten the survival of the red blood cells but also damage vital tissues such as the kidney, heart and brain, leading ultimately to organ failure. At present the only available treatments are blood transfusions and drugs to relieve pain.

While the molecular basis of sickle cell ("S-S") disease has been delineated, the exact pathophysiology of the vasoocclusive crises has never been adequately defined. There is little clinical correlation between the degree of hemolysis and the incidence or severity of painful crises, suggesting that the mechanisms of the two may be at least in part independent. It is known that erthrocytes which are homozygous for the S hemoglobin gene but are morphologically normal have a tendency to adhere abnormally to vascular endothelium. Drugs that can alter the erythrocyte cell membrane could conceivably decrease this erythrocyte-endothelial cell affinity, thus resulting in decreased vasoocclusion.

The effects of using conventional androgens given to patients with sickle cell disease have previously been studied and reported. See the following:

(1) Isaacs, W. A. and Hayhoe, F. G. J.: Steroid Hormones in Sickle-Cell Disease, Nature 215: 1139–1142, 1967;

(2) Mentzer, W. C.; August, C. S., and Nathan, D. G.: The Effects of Androgen Administration in Sickle Cell Anemia, Pediat. Res. 3: 378, 1969;

(3) Raper, A. B.; Black, A. J., and Huntsman, R. G.: Sickling and Steroid Hormones, Trans. Royal Soc. Trop. Med. Hyg. 64(2): 293–295, 1970;

(4) Lundh, B., and Gardner, F. H.: The Haematological Response to Androgens in Sickle Cell Anemia, Scand. J. Haemat. 7: 389–397, 1970;

(5) Isaacs, W. A., Effiong, C. E., and Ayeni, O.: Steroid Treatment in the Prevention of Painful Episodes in Sickle-Cell Disease, Lancet pp. 570–571, Mar. 11, 1972; and (6) Adadfvoh, B. K. and Isaacs, W. A.: The Effect of Megestrol Acetate on Sickling, AM. J. Med. Sci., 265(5): 367–370, 1973.

Preparations of hormones, dosages and modes of administration were varied in these prior studies. While improvement in hemoglobin levels were seen, discordant results were reported with respect to crises, ranging from a decrease in incidence (see papers 1, 5 and 6 above), to no apparent benefit (see papers 2–4) and in men there was an increase in epsiodes of painful priapism (paper 4).

The present invention is based on the finding that danazol can be used with significant benefit in the treatment of sickle cell disease. The effects obtained with the invention represent a significant improvement over the previous reported results using conventional androgens.

Danazol is known chemically as 17-pregna-2,4-dien-20yno[2,3-d]-isoxazol-17-ol; 17a-pregn-4-en-20-yno[2,3-d]-isoxazol-17-ol; 1-ethynyl-2,3,3a,3b,4,5,10,10a,11,12,-12a-dodecahydro-10a-12a-dimethyl-1H-cyclopenta-[7,8]-phenanthro[3,2-d]isoxazol-1-ol; or 17-ethynyl-17-hydroxy-4-androsteno-[2,3-d]-isoxazole. See British Pat. No. 905,844 (1962 to Sterling Drug), C.A. 58, 689c (1963); and U.S. Pat. No. 3,135,743 (1964 to Sterling Drug). It is available as "Danocrine" from Winthrop Laboratories and is a synthetic hormone derived from ethisterone. It was originally approved for use in the treatment of endometriosis. Subsequently it has been found to be useful in the treatment of idiopathic thrombocytopenic purpura, autoimmune hemolytic anemia, paroxysmal nocturnal hemoglobinuria and other disorders as described in the earlier applications referred to above and in related papers as follows:

Ahn, Y. S; Harrington, W. J.; Simon, S. R.; Mylvaganam, R; Pall, L. M., and So. A. G.; "Danazol for the Treatment of Idiopathic Thrombocytopenic Purpura", NEJM 308: 1396–1399, 1983;

Ahn, Y. S.; Mylvaganam, R.; Garcia R. O.; Kim, C. I.; Palow, D., and Harrington, W. J.: "Low Dose Danazol Therapy in Idiopathic Thrombocytopenic Purpura", Ann. Int. Med., 1986 (accepted);

Ahn, Y. S.; Harrington, W. J.; Ayub, J., Mylvaganam, R., and Pall, L. M.: "Danazol Therapy for Autoimmune Hemolytic Anemia", Ann. Int. Med. 102: 298–301, 1984;

Harrington, W. J.; Ahn, Y. S.; Cohen, J. J.; Ayub, J., and Pall, L. M.: "Treatment of Paroxysmal Nocturnal hemoglobinuria with Danazol", presented at the Twentieth Congress of the International Society of Hematology, Buenos Aires, Argentina, September 1984 (Abstract);

Harrington, W. J.; Ahn, Y. S.; Cohen J. J.; Ayub, J., and Pall, L. M.: "Treatment of Paroxysmal Nocturnal Hemoglobinuria with Danazol", presented at the Annual Meeting of the American Society of Hematology, December 1984, Blood 64 (5): 253a.

The amount of danazol administered for present purposes can be varied and the optimum to use in any particular situation can be readily determined. Typical dosages may be in the order of 10–500 mg administered one or more times daily depending on the seriousness of the condition, the health, sex and age of the patient, as well as other factors. For most adult patients an oral dose of 200 mg two or four times a day may be given as an example although it will be recognized that other dosages may be used depending on the circumstances. These dosages may be in conventional form suitable for oral or injectable administration, e.g., tablets, capsules, syrups, sterile solutions, or suspensions and the like.

The invention and its advantages are illustrated by tests carried out on six patients suffering from sickle cell disease (S-S disease). These patients had been previously given clinical trials of other agents, with no benefit. Each of the patients was experiencing at least one painful crisis a month. In addition, one of the patients had had, over a six month period, daily episodes of painful priapism lasting two to three hours.

Danazol was administered in a dosage of 200 mg three times daily. The results are summarized in Table 1.

TABLE 1

| | Response to Danzol Therapy in Six Patients | | | | | | | | | |
|---|---|---|---|---|---|---|---|---|---|---|
| | Painful/Crisis Average/Month | | Duration of Treatment | Hemoglobin (mg/dl) | | Reticulocyte Count (%) | | MCHC (g/dl) | | Haptoglobin (mg/dl) | |
| Pt. | Before | After | Weeks | Before | After | Before | After | Before | After | Before | After |
| 1 | 1 | 0 | 24 | 8.0 | 8.6 | 26 | 15 | 35 | 33 | <5 | <5 |
| 2 | 2 | 0 | 32 | 8.8 | 10.7 | 20 | 4 | 35 | 31 | <5 | 70 |
| 3 | 2 | 0.3 | 41 | 9.1 | 10.6 | 24 | 9 | 33 | 34 | <5 | <5 |
| 4 | 2 | 0.5 | 31 | 8.1 | 9.8 | 18 | 7 | 33 | 32 | <5 | <5 |
| 5 | 2 | 0.4 | 20 | 8.1 | 9.8 | 21 | 3 | 34 | 33 | <5 | 85 |
| 6 | 1 | 0.3 | 17 | 7.0 | 8.7 | 20 | 4 | 33 | 34 | <5 | 44 |

The results tabulated above show marked symptomatic benefit in the use of danazol for the treatment of S-S disease. Particularly significant is the decrease of 85% in incidence of painful crises.

In addition to the indicated amelioration of crises, each patient noted improvement in sense of well-being and a substantial decrease in narcotic requirement. Especially dramatic was the prompt relief of chronic recurrent priapism in patient number five. Some benefit was also apparent in hematological parameters.

The manner in which the danazol functions to benefit patients with sickle cell anemia is not fully understood. However, danazol is beneficial in the treatment of autoimmune hemolytic anemias and paroxysmal nocturnal hemoglobinuria and it appears that a feature common to the pathogenesis of these anemias is red cell membrane modification. It is considered that by using danazol in the treatment of sickle cell disease the red cell membranes can be favorably modified in the direction of decreasing the fragility of the red cells while increasing their deformability thereby favoring improved red cell survival with the indicated clinical benefit. The results obtained appear to be unique to the case where danazol is used, apparently because of the special affinity it has for red cell membranes so as to make them less fragile and more pliable. The compound appears to be better suited than conventional androgens for use in females as well as males. It has few side effects when used and appears to offer the first practical long term management of sickle cell disease.

The scope of the invention is defined in the following claim wherein:

1. A method of treating sickle cell anemia which comprises administering to a person in need of such treatment, an effective amount of danazol.

* * * * *